Figure 1:
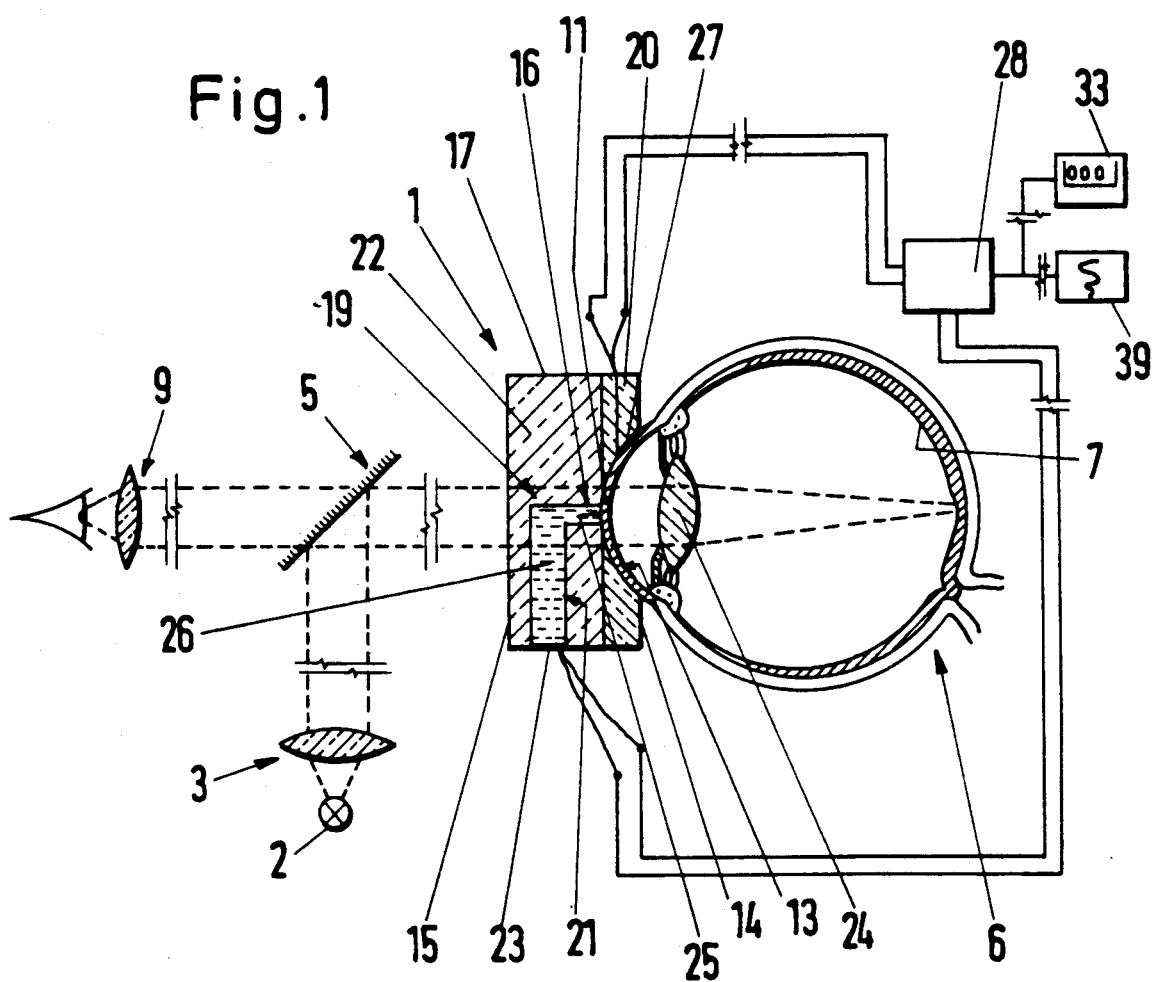

United States Patent [19]  
Robert

[11] Patent Number: 5,032,020  
[45] Date of Patent: Jul. 16, 1991

[54] OPHTHALMOLOGICAL INSTRUMENT

[76] Inventor: Yves Robert, Susenbergstrasse 24, 8044 Zürich, Switzerland

[21] Appl. No.: 288,097

[22] Filed: Dec. 22, 1988

[30] Foreign Application Priority Data

Feb. 9, 1988 [CH] Switzerland .................. 466/88

[51] Int. Cl.⁵ ..................... A61B 3/00; A61B 3/16
[52] U.S. Cl. .......................... 351/219; 128/645
[58] Field of Search ............ 351/219, 221; 128/646, 128/645, 648, 652

[56] References Cited

U.S. PATENT DOCUMENTS 3,929,124 12/1975 Yablonski et al. ............. 351/219
4,628,938 12/1986 Lee ............................ 128/652

FOREIGN PATENT DOCUMENTS 3421701 6/1984 Fed. Rep. of Germany.

OTHER PUBLICATIONS

IEEE Transactions on Biomedical Engineering, vol. BME-29, No. 3 Mar. 1982, pp. 178-183.

A New Applanation Ophthalmo-Tonometer, Edward B. Coburn M.D., Apr. 1908, pp. 447-450.

Primary Examiner—Paul M. Dzierzynski  
Attorney, Agent, or Firm—Brady, O'Boyle & Gates

[57] ABSTRACT

The ophthalmological instrument serves for examining the background (7) of the eye with simultaneous determination of intraocular pressure. A transparent contact member (1) has a concavely curved surface (13) adapted to the curvature of the cornea (11) of the eye (6). In the center of this curved surface (13), a transparent pressure transmitting element (25) is arranged which acts on a pressure sensor (23) by way of a cavity (19) filled with a liquid (26). The contact member (1) is designed as an imaging optical component forming together with the observation optic (9) an observation device for examination of the eye background (7). Additional pressure sensors (27) are located at the rim of the concave curvature (13) of the contact member (1), these additional pressure sensors, on the one hand, monitoring an exact positioning of the contact member (1) and, on the other hand, eliminating falsification of the measured value, caused by the contact pressure of the contact member (1) against the eye (6), by means of an electronic measuring data evaluation.

6 Claims, 2 Drawing Sheets

OPHTHALMOLOGICAL INSTRUMENT

The invention relates to an ophthalmological instrument with a contact member to be pressed against the cornea of the eye and designed as an imaging component, by mean of which the background of the eye can be illuminated and observed.

Such an ophthalmological instrument is used, with a contact member as a fundus contact lens according to Goldmann worldwide in ophthalmology, for example in order to illuminate, with the aid of a slit lamp, a condenser system and a partially reflecting mirror, the background of the eye and to examine the latter by way of a viewing optic. The contact lens has a concave surface adapted to the curvature of the cornea and thereby reduces reflections by the illumination on the surface of the cornea and, respectively, the surface of the contact lens. Together with the surface lying in opposition to this adapted surface, the contact lens forms, as an optical component, a lens within the entire illumination and observation system.

Measurement of intraocular pressure is possible at present only by means of an applanation tonometer (pursuant to the Imbert-Fick law, 1885) wherein a transparent pressure member with a planar contact surface is pressed against the curved cornea in such a way that the latter is flattened over an area of approximately 7 mm². Before performing the measurement, a strip of fluorescein paper is inserted in the conjunctival sac. During the measurement, the eye is illuminated by a slit lamp with blue filter. In the zone of the contact surface of cornea and pressure member, the film of tears which contains fluorescein and shines green-yellowish in the blue light is displaced so that the boundary between flattened and curved cornea is readily identifiable. The contact pressure required for flattening is a measure for intraocular pressure.

Thus far, the following tests, inter alia, could not be performed at all or could be conducted even with the collaboration of an assistant only in a cumbersome and/or inaccurate fashion:

Measurement of pulsating intraocular pressure in order to obtain information regarding certain cerebrovascular diseases.

Tonography wherein the intraocular pressure is artificially raised by a suction cup applied laterally to the eye, the suction cup is removed, and then the intraocular pressure is measured repeatedly at brief time intervals. Although the method of tonography has become obsolete nowadays since it is too complicated and too inaccurate by means of the instruments available at present, its theoretical value is irrefutable.

Ophthalmodynamometry wherein eye pressure is vigorously increased by means of the above-mentioned suction cup in order to determine cerebrovascular blood pressure by the pulsing actions of the retinal vessels at the background of the eye with simultaneous measurement of the eye pressure. This measurement is of eminent significance for the identification of cerebrovascular disturbances. Thus far, this method could be performed only indirectly and only by a team of two persons in clinics.

Photopapillometry (EP-A 136440) wherein the intraocular pressure is only slightly raised, and the brightness of the optic nerve (blind spot) and its change under artificial pressure increase are determined by means of a photopapillometer (reflection measuring device). This permits gaining information o the development or the course of glaucoma.

In order to avoid measuring errors, tonometry (measurement) must be performed over the corneal center of the eye. Heretofore, it has been impossible to simultaneously observe the eye background. One could either observe the background of the eye, or one could measure the pressure, but not both at the same time.

The invention solves the problem of measuring the intraocular pressure simultaneously while observing the eye beackground.

The advantages attained by the invention are to be seen essentially in that some eye examinations, such as the ones mentioned above, inter alia, can be performed without increased expenditure in apparatus and personnel in a greatly simplified manner and by only one person without additional auxiliary means, and that other examinations, such as tonography, for example, can be performed with the required accuracy solely on account of the ophthalmological instrument of this invention.

Figure 2:
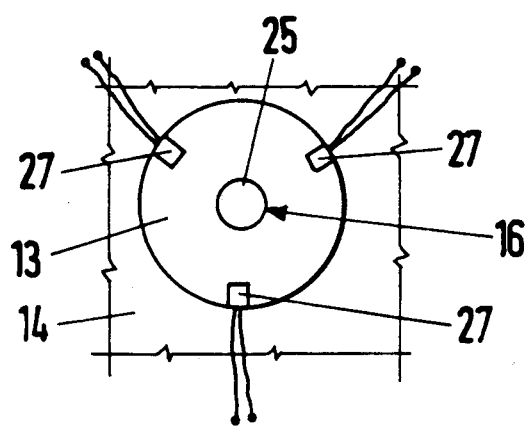
Figure 3:
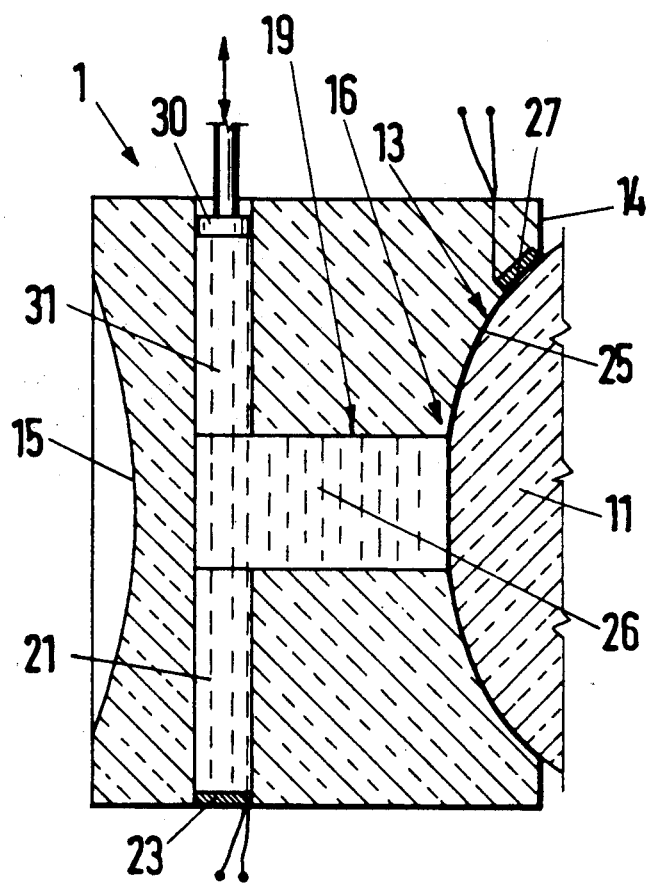
Figure 4:
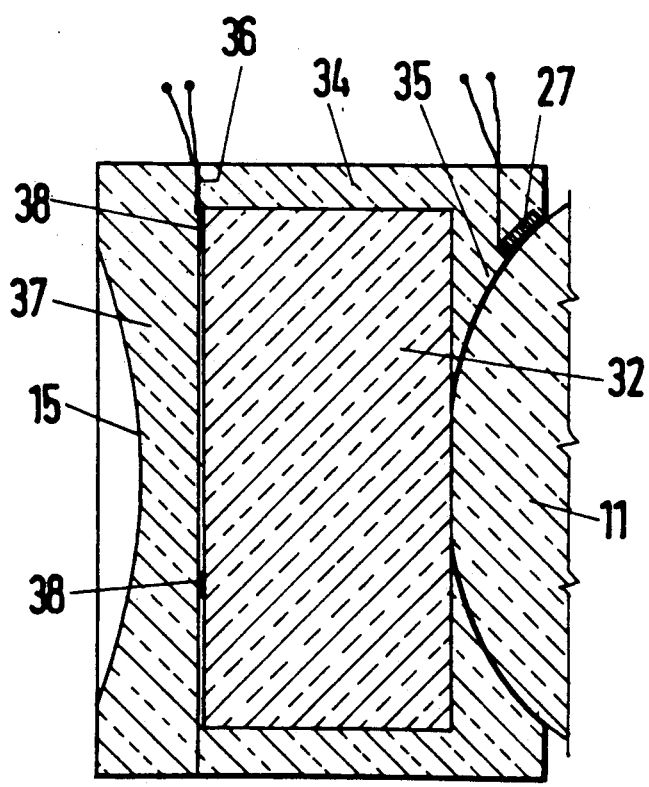

The invention will be described in greater detail below with reference to the appended drawings showing merely exemplary embodiments wherein:

FIG. 1 is a sketch, in principle, of the optical beam path with a longitudinal section through an ophthalmological instrument according to the invention, FIG. 2 is a top view of the contact member of the instrument according to FIG. 1, FIG. 3 is a longitudinal section through a modification of the contact member, FIG. 4 is a longitudinal section through a second modification of the contact member.

In FIG. 1, the eye background 7 is illuminated through an approximately cylindrical contact member 1 with the aid of a slit lamp 2, a condenser system 3, and a partially reflecting mirror 5, and examined by way of an observation optic 9. The purpose of this contact member 1 resides in extensively eliminating the light reflection on the surface of the cornea 11. The surface 13 of the contact member 1 facing the eye 6 is concave in a rotationally symmetrical fashion and is adapted, in the contact zone with the cornea 11, in its curvature to the curvature of the cornea 11 of the eye 6. Outside of the contact zone, the surface 13 passes over into a planar cylinder base surface 14. The surface 15 lying in opposition to the surface 13 is planar, provided with an antireflection coating and extends perpendicularly to the axis of symmetry of surface 13; however, this surface 15 can also be a spherical or aspherical, rotationally symmetrical surface. The surface 15 is adapted to the optical requirements for illumination and observation of the eye background 7. The lateral boundary of the contact member 1, preferably designed as a cylindrical-shell surface 17, does not need to meet any optical requirements.

In the center of surface 13 an opening 16 of a cavity 19 is arranged, this cavity extending at an angle as a duct 21 to the cylindrical-shell surface 17 and being connected to the latter in a leakproof fashion by means of a pressure sensor 23. The cavity 19 and the duct 21 are filled entirely and without gas bubbles with a liquid 26 having at least approximately the same refractive index as the material of the contact member 1.

The opening 16 of the cavity 19 is closed, on the side facing the cornea 11, with a transparent membrane 25 (see also FIG. 3). The opening 16 sealed by the membrane 25 preferably has a diameter of 3 mm (corresponding to a measuring area of 7 mm²).

Three pressure sensors 27 (FIG. 2) for measuring the contact pressure of the contact member 1 against the eye 6 are located at equal mutual angular spacings at the rim of the surface 13 outside of the optically utilized region.

According to FIG. 1, the contact member 1 is composed of two cylindrical parts 20 and 22 for a simpler mounting of the membrane 25, the surfaces 13 and 14 pertaining to part 20, and the surface 15 pertaining to part 22. The membrane 25 lies between the planar interfaces of these parts 20, 22. Both interfaces are glued together with an adhesive having at least approximately the same refractive index as the two cylindrical parts 20, 22.

In an eye examination, the contact member 1 is pressed against the cornea 11, namely in such a way that the opening 16, closed by the membrane 25, is located in the center of the cornea 11. The cavity 19 is filled entirely with a liquid 26 and is hermetically sealed. Since the membrane 25 on the opening 16 retains its planar surface during the pressure contact, the cornea 11 is flattened (applanation). The intraocular pressure then exerts a force on the membrane 25 by way of the cornea 11, and the membrane, in turn, exerts pressure on the liquid 26 in the cavity 19. Since any liquid 26 is incompressible, and the pressure sensor 23 does not experience any noticeable change in volume, either, the pressure of the liquid 26 on the walls of the cavity 19 and on the pressure sensor 23 is equal to the intraocular pressure, with the known limitation that the latter has been increased by the applanation by about 2%.

The only relevant measuring error that can still arise is caused by the pressure contact of the contact member 1 against the eye 6. Differently strong contact pressure leads to a differently great increase in intraocular pressure. This error is eliminated as follows. The contact pressure is measured by the three pressure sensors 27, and the differences of the measured values are determined by an electronic evaluating circuit 28. With sufficiently coinciding measured values, an average value is formed from the three measured values, and this average value is utilized with the measured value of the pressure sensor 23 for the automatic calculation of the actual intraocular pressure and is displayed by an indicator arrangement 33. By the connection of a printer 39 to the electronic circuit 28, the chronological pressure curve can be illustrated.

In case of differing measured values of the three pressure sensors 27, the direction or, respectively, coordinate direction is determined, in which the contact member 1 is to be moved.

Illumination of the eye background 7 takes place, as illustrated schematically in FIG. 1, from the lamp 2 via the condenser system 3, the partially reflecting mirror 5, the contact member 1, through the cornea 11 and the lens 24 of the eye. The examination takes place via the observation optic 9, likewise via the partially reflecting mirror 5 and then in analogy to the observation beam path. Since the contact member 1 is designed as an imaging optical component, and since the pressure sensor 23 as well as the three pressure sensors 27 lie outside of the beam path, there is no impairment of illumination and observation.

For the accurate determination of eye pressure, the opening 16, covered by the membrane 25, is to make contact tangentially in the center of the cornea 11. The cavity 19 filled entirely with liquid 26 is perfectly sealed by the membrane 25. Flawless pressure transmission from intraocular pressure via the cornea 11, the membrane 25 in contact therewith, and through the liquid 26 to the pressure sensor 23 takes place only if there are no gas bubbles in the liquid 26. As described above, the membrane 25 can be clamped in place and mounted between the two parts 20 and 22 of the contact member 1, or the membrane can be glued directly to the curved surface 13. The latter version poses more stringent requirements regarding manufacture since there is otherwise the danger that the glued-on film will be detached along the opening 16.

However, the membrane 25 can also be merely placed between the two parts 20 and 22, and the two parts 20 and 22 can be clamped together with a tightening mechanism, not shown. This version has the advantage that it can be readily taken apart for disinfecting.

As shown in FIG. 3, a cylindrical bore 31, sealed by a plunger 30 as a displacement member, can extend into the cavity 19 from the lateral surface 17. By shifting this plunger 30, the planarity and/or curvature of the membrane 25 can then be adjusted above the opening 16. The cylindrical bore 31 with the plunger 30 facilitates mounting of the membrane 25 since, after mounting, there are still possibilities of correcting the membrane curvature. The cylindrical bore 31 with the plunger 30 can also be utilized as a variant in the above-described bipartite contact member 20, 22 (FIG. 1).

The sensor 23 is preferably located on the cylinder wall 17 because of simple mounting, but it can be arranged at any desired point on the wall of the cavity 19 outside of the illumination and examination ray beam.

The cavity 19, sealed by the membrane 25 and filled with the liquid 26 for pressure transmission to the pressure sensor 23 can be modified so that a transparent cylindrical body 32 (FIG. 4) having adequate optical homogeneity can be fitted into the cavity with clearance adaptation. In this case, the cylindrical contact member likewise exhibits a concave surface 35 analogous to the surface 13. The cavity has a cylindrical shape, and its diameter is of such a size that the defining walls lie outside of the bundle of rays. A circular ring surface 36 opposing the curved surface 35 is closed off by a planar disk 37 having adequate optical quality. The disk 37 carries on its optically unused rim within the circular ring at equal spacings three identical pressure sensors 38 similar in their mode of operation to pressure sensor 23. The cornea 11 in this case presses directly on the body 32, and the latter presses on the pressure sensors. In order to avoid interfering light reflections, the surfaces of body 32 and disk 37 are preferably provided with an antireflection coating.

In a modification, the transparent body 32 can also be designed as part of a lever arm (not shown), and pressure measurement can be performed with a pressure sensor in the proximity of the fulcrum of the lever arm to increase measuring sensitivity. In this construction, care should be taken that the path of the lever arm during pressure contact of the measuring plate against the cornea of the eye is infinitely small. Here again, in order to avoid interfering reflections, the front and rear faces of the measuring plate must carry an antireflection coating.

I claim:

1. An ophthalmological instrument comprising, a corneal contact member (1) designed as a imaging optical component with a corneal contact surface (13) for contacting the cornea (11) of the eye (6),
a pressure measuring device (19, 21, 23, 25, 26, 27) for determining intraocular pressure,
said pressure measuring device (19, 21, 23, 25, 26, 27) including pressure responsive means (25, 32) arranged at said corneal contact surface (13) of said corneal contact member (1) in order to impress or applanate a part of the cornea (11) of the eye (6),
said corneal contact surface (13) of said corneal contact member (1) having a concave shape approximately adapted to the shape of the eye (6), the concave shape of the corneal contact surface (13) has a rim, and said pressure measuring device (19, 21, 23, 25, 26, 27) for determining intraocular pressure includes a first pressure sensor (23) for measuring the pressure exerted by the cornea (11) of the eye on said pressure responsive means (25, 32), at least a second pressure sensor (27) arranged adjacent said rim of said concave shape corneal contact surface (13) for measuring the contact pressure of said contact member (1) against the eye (6), and an electronic evaluating circuit (28) calculating the difference of the electric signals from the first (23) and the second (27) sensor, or the difference between the signal of the first sensor (23) and the average value of the signals from the second sensors (27), wherein a display means (33, 39) is provided which indicates this difference directly and/or the eye pressure determined from this difference.

2. An ophthalmological instrument comprising, a corneal contact member (1) designed as an imaging optical component with a corneal contact surface (13) for contacting the cornea (11) of the eye (6),
a pressure measuring device (19, 21, 23, 25, 26, 27) for determining intraocular pressure including a pressure sensor (23),
said pressure measuring device (19, 21, 23, 25, 26, 27) including a pressure transmitting member (25, 32) arranged at said corneal contact surface (13) of said corneal contact member (1) in order to impress or applanate a part of the cornea (11) of the eye (6), and including a cavity (19) in said corneal contact member (1),
said pressure transmitting member (25, 32) connected to seal off said cavity (19) in said corneal contact member (1),
said cavity being filled entirely with a transparent liquid (26), the index of refraction of the liquid (26) being at least approximately equal to that of the corneal contact member (1),
said pressure sensor (23) connected with said cavity (19) to be acted upon by said liquid (26), said corneal contact member (1) has a side surface (17) beyond said corneal contact surface (13), said cavity (19) extends to said side surface (17), and a plunger means (30) is provided in said cavity (19) at said side surface (17).

3. An ophthalmological instrument, comprising
a corneal contact member (1) with a corneal contact surface (13) to be pressed against the cornea (11) of the eye (6),
said corneal contact member (1) being designed as an imaging optical component, through which the background (7) of the eye (6) can be illuminated and observed,
said corneal contact surface (13) of said corneal contact member (1) to be pressed against the eye cornea (11) having a concave shape approximately adapted to the shape of the eye (6), and the concave shape corneal contact surface having an outer rim,
a pressure measuring device (19, 21, 23, 25, 26, 27) for determining intraocular pressure,
said pressure measuring device (19, 21, 23, 25, 26, 27) including a pressure responsive means (25; 32) arranged at said corneal contact surface (13) of said corneal contact member (1) in order to impress or applanate a part of the cornea (11) of the eye.
said pressure measuring device (19, 21, 23, 25, 26, 27) for determining intraocular pressure including a first pressure sensor (23) for measuring the pressure exerted by the impressed or applanated part of the cornea (11) of the eye on said pressure responsive means (25, 32), at least a second pressure sensor (27) arranged adjacent said rim of said concave shape corneal contact surface (13) for measuring the contact pressure of said contact member (1) against the eye (6), and an evaluation or calculation means (28) for determining the intraocular pressure as the difference of the pressure of the impressed or applanated part of the cornea (11) of the eye (6) on said pressure responsive means (25, 32) and the contact pressure of said contact member (1) against the eye (6) from said at least one second pressure sensor (27).

4. An ophthalmological instrument according to claim 3, wherein said at least one second pressure sensor (27) includes wherein said at least one second pressure sensor (27) includes plural second pressure sensors (27) arranged adjacent said rim of said concave shape corneal contact surface (13), said evaluation or calculation means (28) for determining the intraocular pressure has a electronic evaluating circuit (28) for calculating the difference of the electric signals from said first sensor (23) and said second sensors (27), or the difference between the signal of the first sensor (23) and the average value of the signals from the said second sensors (27), and a display means (33, 39) connected to said electronic evaluating circuit (28) which indicates this difference directly and/or the eye pressure determined from this difference.

5. An ophthalmological instrument according to claim 4, in which at least three of said second sensors (27) are arranged with at least approximately identical angular spacings from one another adjacent the rim in the concave corneal contact surface (13), and that the display means (33, 39) with said electronic evaluating circuit (28) indicates, with adequately mutually coinciding signals of these three pressure sensors (27), the position of the corneal contact member (1) centered with respect to the eye (6) and, with differing signals of these three sensors (27), the direction or coordinate directions in which corneal contact member (1) is to be shifted into its position centered with respect to the eye (6).

6. An ophthalmological instrument, comprising
a corneal contact member (1) with a corneal contact surface (13) to be pressed against the cornea (11) of the eye (6),
said corneal contact member (1) being a rigid transparent member designed as an imaging optical component, through which the background (7) of the eye (6) can be illuminated and observed,
said corneal contact surface (13) of said corneal contact member (1) to be pressed against the eye cornea (11) having a concave shape approximately adapted to the shape of the eye (6), and the concave shape corneal contact surface having an outer rim, a pressure measuring device (19, 21, 23, 25, 26, 27) for determining intraocular pressure, a cavity (19) in said corneal contact member (1), said cavity (19) extending to an opening (16) in said corneal contact surface (13), said opening (16) being sealed off by a transparent membrane (25), said transparent membrane (25) on the opening (16) having a planar surface, said cavity (19) being filled entirely with a transparent liquid (26), the index of refraction of the liquid (26) being at least approximately equal to that of the corneal contact member (1), said pressure measuring device (19, 21, 23, 25, 26, 27) for determining intraocular pressure including a pressure sensor (23) arranged in said cavity (19) for measuring the pressure of said liquid (26), said cavity (19) being sealed off in a leakproof fashion, so that the membrane (25) on the opening (16) retains its planar surface during the pressure contact of said corneal contact surface (13) of said corneal contact member (1) to the eye cornea (11), whereby the part of the eye cornea (11) contacting the membrane (25) being applanated and the intraocular pressure exerting a force on the membrane (25) and by way of said liquid (26) on said pressure sensor (23) arranged in said cavity (19).

* * * * *